(12) United States Patent
Fang

(10) Patent No.: US 9,480,501 B2
(45) Date of Patent: Nov. 1, 2016

(54) MODULAR PEDICLE SCREW

(71) Applicant: BLACKSTONE MEDICAL, INC., Lewisville, TX (US)

(72) Inventor: Samuel Fang, Plano, TX (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 16 days.

(21) Appl. No.: 14/059,203

(22) Filed: Oct. 21, 2013

(65) Prior Publication Data

US 2015/0112390 A1 Apr. 23, 2015

(51) Int. Cl.
*A61B 17/70* (2006.01)

(52) U.S. Cl.
CPC .................. *A61B 17/7037* (2013.01)

(58) Field of Classification Search
CPC combination set(s) only.
See application file for complete search history.

(56) References Cited

U.S. PATENT DOCUMENTS

| | | | |
|---|---|---|---|
| 920,188 A | 5/1909 | Schumacher | |
| 2,987,080 A | 6/1961 | Chandler et al. | |
| 3,477,486 A | 11/1969 | Modrey | |
| 5,505,732 A | 4/1996 | Michelson | |
| 5,797,911 A | 8/1998 | Sherman et al. | |
| 6,485,491 B1 | 11/2002 | Farris et al. | |
| 7,250,052 B2 | 7/2007 | Landry et al. | |
| 7,338,491 B2 | 3/2008 | Baker et al. | |
| 7,377,923 B2 | 5/2008 | Purcell et al. | |
| 7,749,258 B2 * | 7/2010 | Biedermann et al. | 606/308 |
| 7,766,946 B2 | 8/2010 | Bailly | |
| 7,811,310 B2 | 10/2010 | Baker et al. | |
| 7,922,725 B2 | 4/2011 | Darst Rice et al. | |
| 7,942,909 B2 | 5/2011 | Hammill, Sr. et al. | |
| 7,951,173 B2 | 5/2011 | Hammill, Sr. et al. | |
| 8,066,745 B2 | 11/2011 | Kirschman | |
| 8,100,946 B2 | 1/2012 | Strausbaugh et al. | |
| 8,142,436 B2 | 3/2012 | Kirschman | |
| 8,167,910 B2 | 5/2012 | Nilsson | |
| 8,221,472 B2 | 7/2012 | Peterson et al. | |
| 8,419,778 B2 | 4/2013 | Barry | |
| 8,430,914 B2 * | 4/2013 | Spratt et al. | 606/265 |
| 8,882,817 B2 | 11/2014 | Jones et al. | |

(Continued)

FOREIGN PATENT DOCUMENTS

FR 2954689 A1 7/2011
WO 2011/133160 A1 10/2011

OTHER PUBLICATIONS

International Search Report and Written Opinion, PCT/US2012/049180, dated Oct. 26, 2012, 9 pages.

(Continued)

*Primary Examiner* — Jan Christopher Merene
(74) *Attorney, Agent, or Firm* — Baker & McKenzie LLP

(57) ABSTRACT

The present disclosure relates, in some embodiments, to spinal fixation systems that may comprise a bone screw, a body, and a pressure cap. A bone screw may comprise a head at a proximal end, a bone connection element at a distal end, and an external protrusion on a head of a bone screw. A body may comprise a proximal end, a distal end, a mounting rod receiving channel at a proximal end, and a bone screw head receiving channel at a distal end. A portion of the mounting rod receiving channel may be operable to receive a compression element. A pressure cap may comprise a proximal end, distal end, and an internal recess on a distal end. An internal recess may be configured to mate with an external protrusion of a bone screw so as to limit the movement of a bone screw.

38 Claims, 9 Drawing Sheets

(56) References Cited

U.S. PATENT DOCUMENTS

| | | |
|---|---|---|
| 8,951,290 B2 | 2/2015 | Hammer et al. |
| 2002/0120275 A1 | 8/2002 | Schmieding et al. |
| 2003/0105460 A1 | 6/2003 | Crandall et al. |
| 2003/0231927 A1 | 12/2003 | Hale |
| 2004/0176766 A1 | 9/2004 | Shluzas |
| 2004/0186483 A1 | 9/2004 | Bagby |
| 2004/0225289 A1 | 11/2004 | Biedermann et al. |
| 2005/0043735 A1 | 2/2005 | Ahmad |
| 2006/0142762 A1 | 6/2006 | Michelson |
| 2006/0200131 A1 | 9/2006 | Chao et al. |
| 2007/0016200 A1 | 1/2007 | Jackson |
| 2007/0078460 A1 | 4/2007 | Frigg et al. |
| 2007/0118123 A1* | 5/2007 | Strausbaugh et al. .......... 606/61 |
| 2007/0239159 A1 | 10/2007 | Altarac et al. |
| 2007/0281274 A1 | 12/2007 | Schraffran et al. |
| 2008/0009862 A1 | 1/2008 | Hoffman |
| 2008/0147129 A1 | 6/2008 | Biedermann et al. |
| 2009/0076552 A1* | 3/2009 | Tornier .......................... 606/264 |
| 2009/0198280 A1* | 8/2009 | Spratt et al. ................... 606/267 |
| 2009/0281550 A1 | 11/2009 | Keller |
| 2009/0306721 A1 | 12/2009 | Kirschman |
| 2010/0152785 A1* | 6/2010 | Forton et al. ................. 606/301 |
| 2010/0212460 A1 | 8/2010 | Buss et al. |
| 2010/0298891 A1* | 11/2010 | Jackson ......................... 606/308 |
| 2010/0305621 A1* | 12/2010 | Wang et al. ................... 606/305 |
| 2010/0312288 A1 | 12/2010 | Hammill, Sr. et al. |
| 2011/0046683 A1 | 2/2011 | Biedermann et al. |
| 2011/0077694 A1 | 3/2011 | Biedermann et al. |
| 2011/0152940 A1 | 6/2011 | Frigg et al. |
| 2011/0160778 A1 | 6/2011 | Elsbury |
| 2011/0172714 A1 | 7/2011 | Boachie-Adjei et al. |
| 2011/0178559 A1* | 7/2011 | Barry ............................ 606/302 |
| 2011/0263945 A1 | 10/2011 | Peterson et al. |
| 2011/0282399 A1 | 11/2011 | Jackson |
| 2012/0031792 A1 | 2/2012 | Petit |
| 2012/0046699 A1 | 2/2012 | Jones et al. |
| 2013/0096624 A1* | 4/2013 | Di Lauro et al. ............. 606/279 |
| 2013/0110176 A1 | 5/2013 | Rezach et al. |
| 2013/0131734 A1 | 5/2013 | Longtain et al. |
| 2013/0226243 A1* | 8/2013 | Kraus ............................ 606/264 |
| 2015/0272627 A1 | 10/2015 | Jackson |

OTHER PUBLICATIONS

International Search Report and Written Opinion, PCT/US2014/061293, dated Jan. 23, 2015, 12 pages.

U.S. Office Action, U.S. Appl. No. 13/196,635, dated May 8, 2015, 28 pages.

U.S. Office Action, U.S. Appl. No. 14/037,011, dated Jun. 5, 2015, 30 pages.

U.S. Office Action, U.S. Appl. No. 14/092,154, dated Dec. 24, 2015, 11 pages.

U.S. Office Action, U.S. Appl. No. 14/037,011, dated Apr. 21, 2016, 30 pages.

* cited by examiner

MODULAR PEDICLE SCREW

FIELD OF THE DISCLOSURE

The present disclosure relates, in some embodiments, to modular pedicle screws. More specifically, the present disclosure relates, in some embodiments to modular pedicle screws for use in spinal fixation systems.

BACKGROUND OF THE DISCLOSURE

Various systems exist for connecting fastener elements (e.g., pedicle screws) to bones for the purposes vertebral fixation. Such systems may use a plurality of bone screws fitted in bodies, wherein a plurality of bodies are aligned using a mounting rod.

A spinal fixation system may comprise several components with various degrees of stability or various degrees of movement between the components themselves or between the components and the bones to which they are affixed. For example, the connection between the bones and the fastener may have a degree of stability. Greater stability may help promote a more secure system and a more secure fixation for multiple segments of the spine. However, overly rigid or inflexibly positioned fastener elements may prevent the mounting rod from being aligned properly along a plurality of vertebrae.

For surgical proceedings, the components intended to be used for the spinal fixation system may often be preselected. Such selection may be made based on a number of factors such as the particular dimensions of the components and the anatomical location for the fixation of the system. However, sometimes during the actual surgery, the preselected components may be determined to not actually be ideal. This may be the case when the preselected components allow for too much or not enough movement or flexibility of the fastener elements.

SUMMARY

Accordingly, a need has arisen for improved spinal fixation systems that promote secure and stable connections, allow for a desired degree of movement for the fastener elements, and may allow for on-the-spot adjustment or interchangeability of components during surgical procedures. Explained further, it may be desirable to allow or retain a certain degree of movement in the fastener elements so as to promote ideal alignment of the mounting rod through a plurality of bodies in which the fastener elements or bone screws are fitted.

The present disclosure relates, according to some embodiments, to a spinal fixation system that may comprise a bone screw, a body, and a pressure cap. A bone screw may comprise a head at a proximal end, a bone connection element at a distal end, and an external protrusion on the head of the bone screw. A body may comprise a proximal end, a distal end, a mounting rod receiving channel at the proximal end, and a bone screw head receiving channel at the distal end. A proximal end and a distal end may be disposed along a longitudinal axis. A portion of a mounting rod receiving channel may be operable to receive a compression element. A pressure cap may comprise a proximal end, distal end, and an internal recess on the distal end. An internal recess may be configured to mate with an external protrusion of the bone screw so as to limit the movement of the bone screw. The pressure cap may be configured to be disposed within the body and between a mounting rod and a bone screw. A pressure cap may be operable to exert pressure on a bone screw when a mounting rod may be biased against a proximal end of a pressure cap.

In some embodiments, a head of the bone screw may have a substantially spherical surface. In some embodiments, a bone connection element may comprise an external thread operable to be secured into a pedicle portion of a spine. In some embodiments, a bone connection element may have a diameter of about 2.5 mm to about 9 mm, depending on the intended surgical site or other appropriate factors. In some embodiments, a bone connection element may have a length of about 6 mm to 120 mm. In some embodiments, an external protrusion may have a plurality of lateral faces which may form a cross-section with a polygonal shape. In some embodiments, a polygonal shape may be a triangle, rectangle, pentagon, hexagon, heptagon, octagon, or star. In some embodiments, the external protrusion may have a height of about 2 mm to about 5 mm. In some embodiments, a mounting rod receiving channel may be operable to receive a mounting rod at an angle substantially orthogonal to the longitudinal axis of the body. In some embodiments, a bone screw head receiving channel may be sized to securely receive a bone screw head. In some embodiments, a proximal end of the pressure cap may comprise a surface that may be partially curved and may be operable to align with a portion of the cylindrical mounting rod. In some embodiments, a pressure cap may comprise at least one recess disposed along an outer surface of a pressure cap. In some embodiments, an internal recess may pass through from the distal end of a pressure cap to a proximal end of a pressure cap. In some embodiments, a bone screw, a body, a compression element, and a pressure cap may each comprise material independently selected from the group consisting titanium, titanium alloy, stainless steel, cobalt chrome, or any combination thereof. In some embodiments, an internal recess may be configured to limit the movement of the bone screw to that of a mono-axial screw. In some embodiments, an internal recess may limit the pivotal movement of the bone screw to one axis. In some embodiments, a bone screw may have about 30 degrees to about 60 degrees of pivotal movement about the one axis. In some embodiments, an internal recess may have a rectangular shape with a width corresponding to a width of an external protrusion, and a depth sufficient to allow an internal recess to receive an external protrusion. In some embodiments, an internal recess may be configured to mate with an external protrusion of a bone screw to allow poly-axial movement of a bone screw.

The present disclosure relates, in some embodiments, to a bone screw comprising an internal recess disposed on a head of a bone screw. In such embodiments, a pressure cap may comprise an external protrusion formed on a distal end of a pressure cap. Such embodiments differ from the previously described embodiments in that an external member may be located on the pressure cap while an internal recess or a receiving spacing for an external member may be located on a bone screw. One of ordinary skill in the art would appreciate that an internal recess of the bone screw and an external protrusion of a pressure cap may be designed so as to limit the movement of a bone screw. For example, in some embodiments, an internal recess of a bone screw may be designed and configured to limit the movement of a bone screw to that of a mono-axial screw. In some embodiments, an external protrusion may have movement that may be limited to pivotal movement about one axis. Any of the features, variations, and other embodiments described above for the configuration that may comprise an external protrusion on a bone screw and an internal recess on a pressure cap may also be applied to the configuration that may comprise an internal recess on a bone screw and an external protrusion on a pressure cap.

The present disclosure relates, in some embodiments, to methods of affixing a bone screw system to a bone. The method may comprise fitting a bone screw to a body. In assembling a bone screw system, a bone screw may be inserted through a mounting rod receiving channel of a body such that a head may be received and may sit securely in a bone screw head receiving channel. Next, a bone connection element of a bone screw may be fastened or screwed into a bone. The securing of a bone screw may be done through a number of mechanical means. Either before or after a bone connection element may be secured into a bone, a pressure cap may be selected. The selection may be made based on the desired degree of stability of desired degree of movement allowed for a bone screw. A pressure cap may comprise a proximal end, a distal end, and an internal recess formed on the distal end of a pressure cap. An internal recess may be configured to mate with an external protrusion of a bone screw so as to limit the movement of a bone screw. A pressure cap may be fitted on or fitted against a head of a bone screw within the body. Next, a mounting rod may be disposed within a body. A mounting rod may be fitted within a mounting rod receiving channel. A mounting rod may be disposed against the proximate end of a pressure cap. Then, a compression element may be secured within a mounting rod receiving channel. The securing of a compression element may create a compressive force on a mounting rod that may allow a mounting rod to bias against or be pressed down on a pressure cap. Any of the features, variations, and other embodiments described above for the articles and systems of the present disclosure may apply to the presently disclosed method without departing from there description herein.

BRIEF DESCRIPTION OF THE DRAWINGS

Some embodiments of the disclosure may be understood by referring, in part, to the present disclosure and the accompanying drawings, wherein.

DETAILED DESCRIPTION

The present disclosure relates, in some embodiments, to spinal fixation systems. More specifically, the present disclosure relates, in some embodiments, to spinal fixation systems with modular pedicle screws that may allow for poly-axial, mono-axial, and uni-planar movement.

Figure 1:
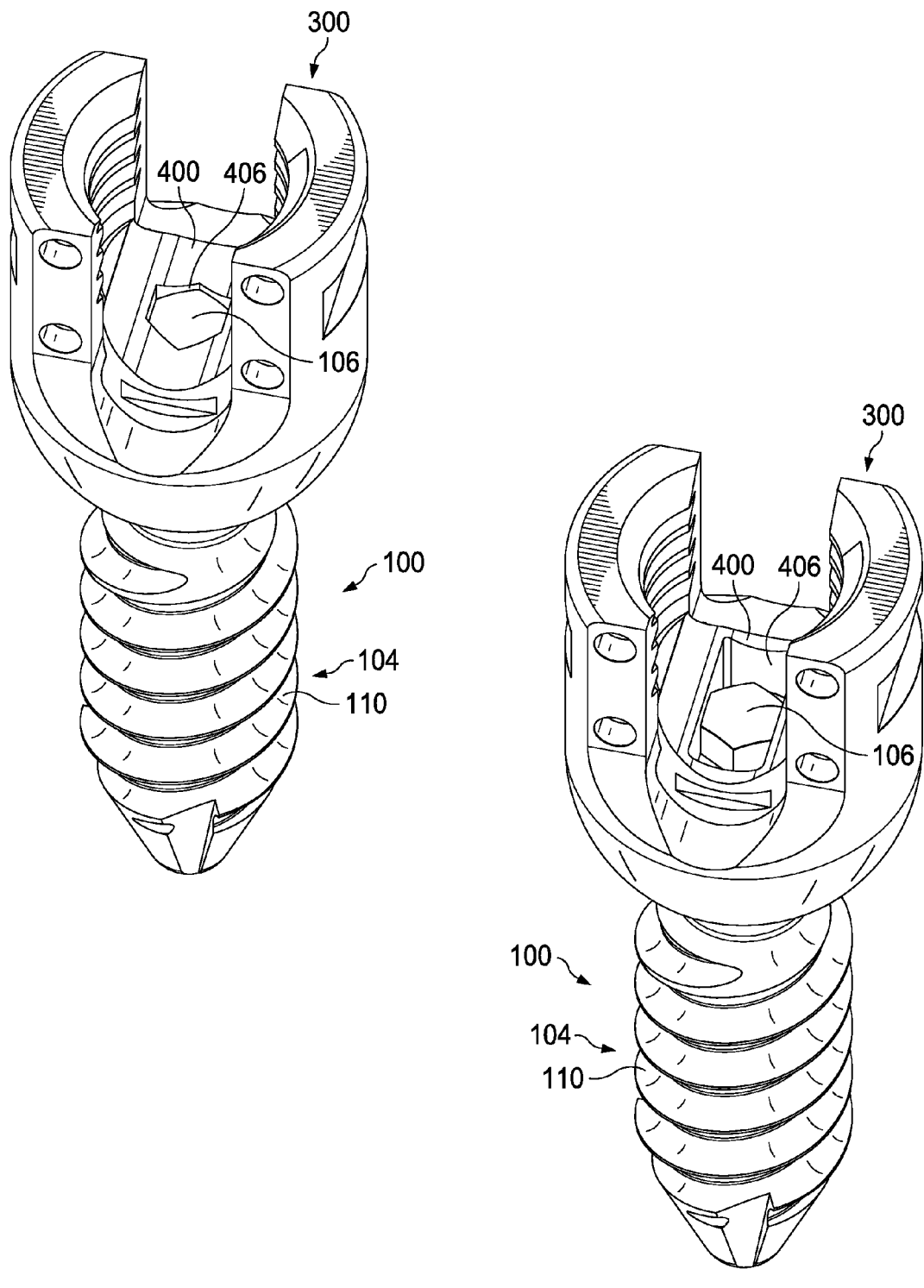
FIG. 1 illustrates a perspective view of two spinal fixation systems according to an exemplary embodiment of the disclosure.

Referring now to FIG. 1, perspective views of two spinal fixation systems according to exemplary embodiments of the present disclosure are shown. As seen in FIG. 1, the spinal fixation systems according to the present disclosure may comprise bone screw 100, body 300, and pressure cap 400. Bone screw 100 may comprise bone connection element 104, which may comprise external thread 110. External thread 110 may allow bone screw 100 and the spinal fixation system to be secured into a bone. Bone screw 100 may further comprise external protrusion 106 which may be configured to fit with internal recess 406 of pressure cap 400. The two example embodiments illustrated in FIG. 1 show how different spinal fixation systems according to the present disclosure may be assembled. The pressure cap 400 illustrated in FIG. 1 may serve to limit the motion and degrees of freedom of bone screw 100.

Figure 2:
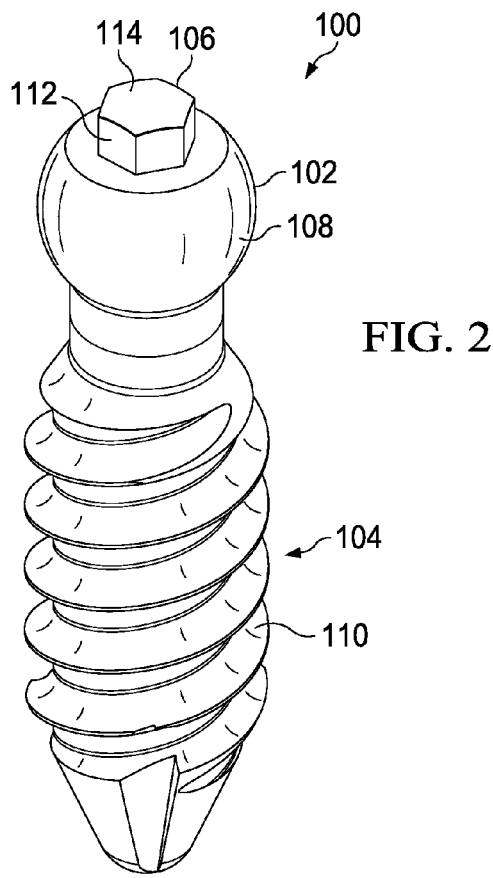
FIG. 2 illustrates a perspective view of a bone screw according to an exemplary embodiment of the disclosure.

Referring now to FIG. 2, a perspective view of bone screw 100 according to an example embodiment of the disclosure is shown. As seen in FIG. 2, bone screw 100 may comprise head 102 at a proximal end and bone connection element 104 at a distal end. Further, external protrusion 106 may be disposed on head 102 of bone screw 100.

Head 102 of bone screw 100 may have substantially spherical surface 108. Head 102 of bone screw 100 may be entirely spherical but for a proximate portion to accommodate external protrusion 106 and a distal portion to accommodate bone connection element 104. The radius of the spherical surface 108 may vary in different embodiments of the present disclosure without departing from the description herein. According to some embodiments, the radius of the spherical surface may be about 3.5 mm to about 12 mm. Bone screws 100 with different sized heads 102, as defined by the radius of spherical surfaces 108, may be more appropriate in different circumstances. For example, bone screw 100 used for the cervical and upper thoracic regions may have a smaller head 102 or a smaller radius for the spherical surface 108. As another example, bone screw 100 used for the lumbar or lower thoracic regions may have a larger head 102 or a larger radius for the spherical surface 108.

Bone connection element 104 of bone screw 100 may comprise external thread 110. External thread 110 may allow bone screw 100 to be secured into a bone. In some embodiments, external thread 110 may be secured into a pedicle portion of a spine. The dimensions of bone connection element 104 along with the pattern and structure of external thread 110 may be varied to achieve different effects without departing from the description herein. For example, bone screws 100 with different lengths or diameters may be more appropriate for different regions of a spine. According to some embodiments of the present disclosure, the spinal fixation system may be secured to a cervical and upper thoracic region. In such embodiments, the major diameter of the bone connection element 104 may range from about 2.5 mm to about 4.5 mm, and the length of the bone connection element 104 may range from about 6 mm to about 30 mm. According to some embodiments of the present disclosure, the spinal fixation system may be secured to a lumbar or lower thoracic region. In such embodiments, the major diameter of the bone connection element 104 may range from about 4 mm to about 9 mm, and the length of the bone connection element 104 may range from about 20 mm to about 120 mm.

External protrusion 106 of bone screw 100 may be disposed on head 102. External protrusion 106 may have a plurality of lateral faces 112 that may form cross-section 114 with a polygonal shape. As seen in FIG. 2, in some embodiments of the present disclosure, external protrusion 106 may have six lateral faces 112, forming cross-section 114 in the shape of a hexagon. According to other embodiments of the present disclosure, the polygonal shape formed by cross-section 114 may be a triangle, rectangle, pentagon, heptagon, octagon, or star-shaped. The number of lateral faces 112 and the polygonal shape of cross-section 114 may vary in different embodiments of the present disclosure without departing from the description herein. Variations in the number of lateral faces 112 and the polygonal shape of cross-section 114 may provide for various advantages. For example, external protrusion 106 with fewer lateral faces 112 may be easier to manufacture. As another example, external protrusion 106 with a particular geometry for the polygonal shape of cross-section 104 may be easier to handle and use during assembly of the spinal fixation system or during surgical procedures.

Dimensions of external protrusion 106, along with lateral faces 112 and cross-section 114 may vary in different embodiments of the present disclosure without departing from the description herein. According to some embodiments of the present disclosure, external protrusion 106 may have a height of about 2 mm to about 5 mm. According to some embodiments of the present disclosure, external protrusion 106 may have a width of about 2.5 mm to about 5 mm. Variations in the dimensions of external protrusion 106 may provide for various advantages. For example, a greater height of external protrusion 106 or lateral faces 112 may allow for a better mating of external protrusion 106 of bone screw 100 with an internal recess 406 of pressure cap 400. As another example, a greater height of external protrusion 106 or lateral faces 112 may allow for greater ease in the handling of bone screw 100 during assembly of the spinal fixation system or during surgical procedures. As yet another example, a greater or lesser width of external protrusion 106 may allow for a more convenient design of internal recess 406 of pressure cap 400, or a more secured mating of external protrusion 106 with internal recess 406 of pressure cap 400. As yet another example, particular dimensions for external protrusion 106 may be more advantageous depending on the intended anatomical location of the spinal fixation system.

Figure 3:
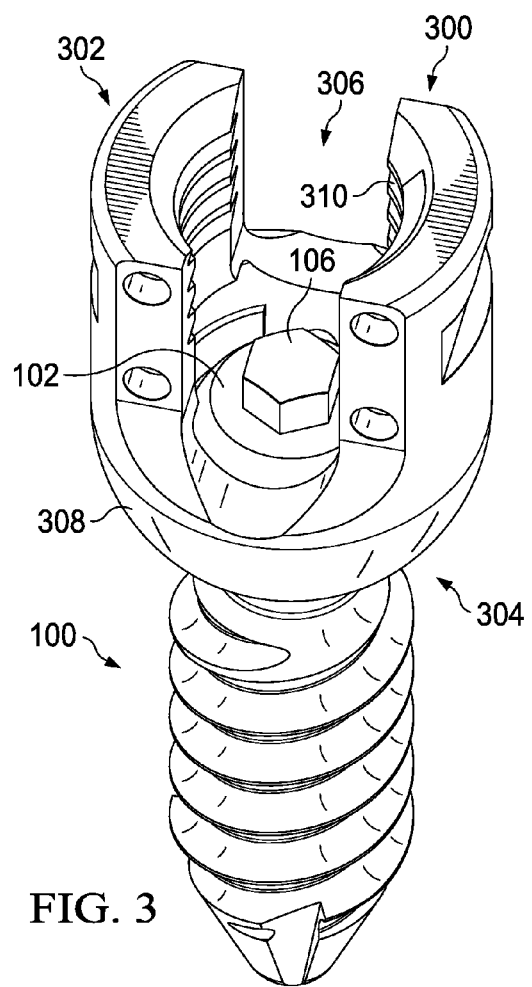
FIG. 3 illustrates a perspective view of a body and a bone screw fitted together according to an exemplary embodiment of the disclosure.

Referring now to FIG. 3, a perspective view of body 300 and bone screw 100 fitted together according to a specific example embodiment of the present disclosure is shown. As seen in FIG. 3, body 300 of the present disclosure may comprise proximal end 302 and distal end 304. Proximal end 302 and distal end 304 may be disposed along a longitudinal axis of body 300. Mounting rod receiving channel 306 may be disposed at proximal end 302 of body 300. Bone screw head receiving channel 308 may be disposed at distal end 304 of body 300.

Figure 7:
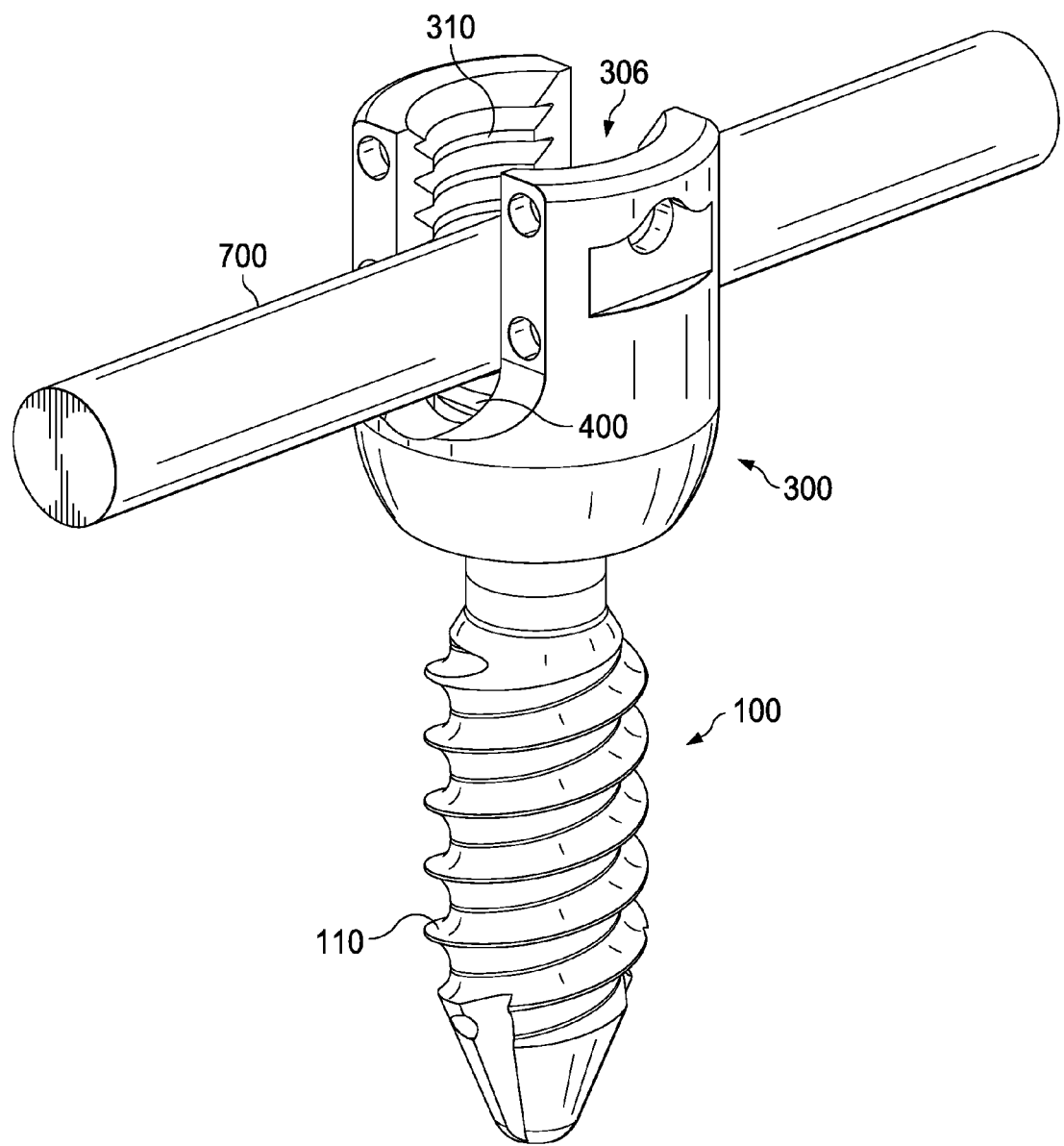
FIG. 7 illustrates a perspective view of a mounting rod, pressure cap, body, and bone screw fitted together according to an exemplary embodiment of the disclosure.

Mounting rod receiving channel 306 disposed on proximal end 302 of body 300 may be operable to receive a mounting rod 700 (see, for example, FIG. 7). The mounting rod 700 may be received in an orientation such that the mounting rod may be substantially orthogonal to the longitudinal axis of body 300. Mounting rod receiving channel 306 may further comprise a proximal portion comprising internal thread 310. Internal thread 310 may be operable for receiving a compression element. The dimensions, pattern, and structure of internal thread 310 may be varied to achieve different effects or provide different advantages without departing from the description herein. For example, different internal threads 310 may allow for compression elements with different external thread to be secured on proximal end 302 of body 300. Different compression elements may be more advantageous depending on the type of stability needed or the intended anatomic location of the spinal fixation system.

Bone screw head receiving channel 308 disposed at distal end 304 of body 300 may be operable to receive head 102 of bone screw 100. Bone screw 100 and body 300 may be selected such that bone screw head receiving channel 308 may be sized to securely receive head 102 of bone screw 100. According to some embodiments of the present disclosure, bone screw head receiving channel 308 may receive head 102 such that spherical surface 108, as seen in FIG. 2, may be substantially enclosed by bone screw head receiving channel 308. As a result, the contact between bone screw head receiving channel 308 and spherical surface 108 may create a secure connection between bone screw 100 and body 300. One of ordinary skill in the art would appreciate that spherical surface 108 may not need to be substantially enclosed in order to create a secure connection between bone screw 100 and body 300. According to some embodiments of the present disclosure, bone screw head receiving channel 308 may receive head 102 such that external protrusion 106 may be substantially exposed. External protrusion 106 may be substantially exposed so that external protrusion 106 may mate or be secured in internal recess 406 of pressure cap 400. According to some embodiments of the present disclosure, bone screw head receiving channel 308 may receive head 102 through a variety of means. For example, in some embodiments, bone screw 100 may be lowered into body 300 and head 102 so that bone screw 100 may directly rest in bone screw head receiving channel 308. As another example, in some embodiments, bone screw head receiving channel 308 may engage with head 102 of bone screw 100 in the manner of a ball and socket joint. Any number of mechanisms may be used to engage bone screw head receiving channel 308 with head 102 of bone screw 100. The mechanism may be varied without departing from the description herein.

One of ordinary skill in the art would appreciate that the type of bone screw 100 and type of body 300 chosen may determine what range of motion or how many degrees of freedom head 102 of bone screw 100 may have in bone screw head receiving channel 308. As seen in FIG. 3, in some embodiments, the fitting of body 300 to bone screw 100 may provide for a bone screw with poly-axial movement. Spherical surface 108 of head 102 of bone screw 100 may be allowed to freely rotate within bone screw head receiving channel 308.

The dimensions of body 300 may be varied to achieve different effects or provide different advantages without departing from the description herein. In some embodiments, the height of the body may range from about 12 mm to about 30 mm. Various advantages may be derived from selecting an appropriately sized body 300. In some embodiments, a larger body 300 may be advantageous so that the larger body size may accommodate larger pressure caps, larger mounting rods, or larger compression elements. In some embodiments, a smaller body 300 may be advantageous so that the smaller body size may be less invasive as part of the spinal fixation system in the patient's body and may provide a flatter or more flush contour against the bones of the spine.

Figure 4A:
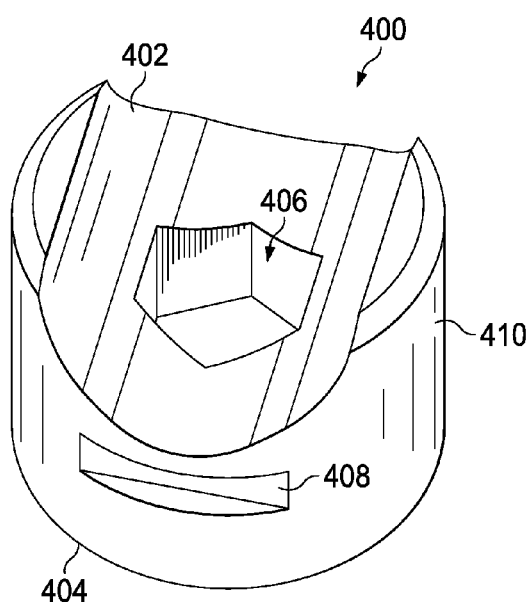
FIG. 4A illustrates a perspective view of a pressure cap according to an exemplary embodiment of the disclosure.
Figure 4B:
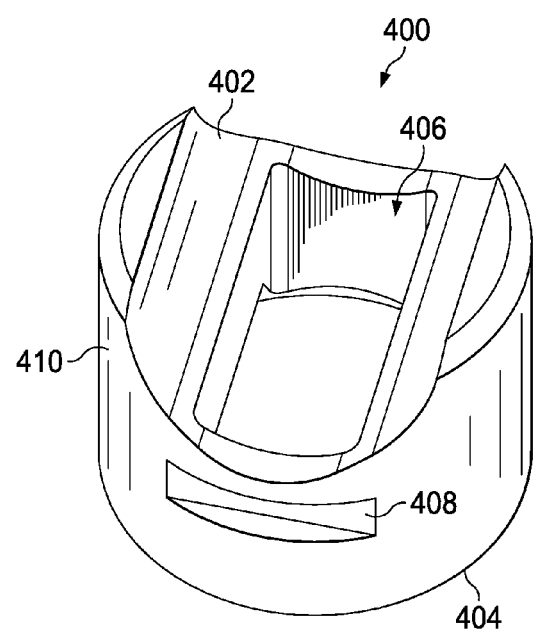
FIG. 4B illustrates a perspective view of a pressure cap according to an exemplary embodiment of the disclosure.
Figure 4C:
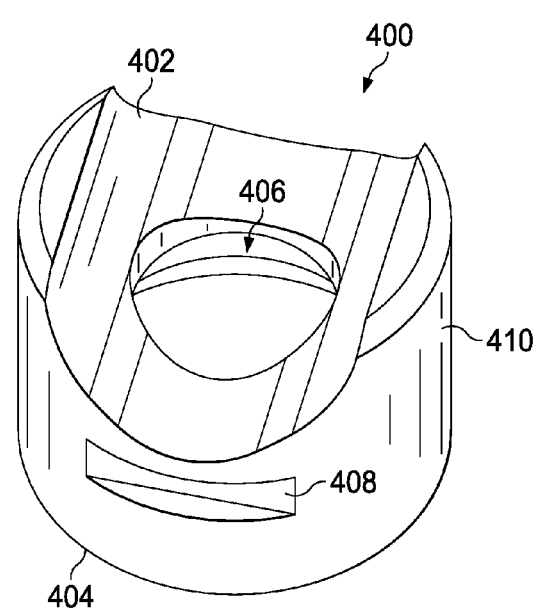
FIG. 4C illustrates a perspective view of a pressure cap according to an exemplary embodiment of the disclosure.

Referring now to FIG. 4A, FIG. 4B, and FIG. 4C, perspective views of three exemplary pressure caps 400 according to specific example embodiments of the present disclosure are illustrated. FIG. 4A illustrates pressure cap 400 that may be operable to limit the movement of bone screw 100 in a spinal fixation system to that of a mono-axial screw. FIG. 4B illustrates pressure cap 400 that may be operable to limit the movement of bone screw 100 in a spinal fixation system to that of a uni-planar screw. FIG. 4C illustrates pressure cap 400 that may be operable to allow for poly-axial movement of bone screw 100. The example embodiments of pressure caps 400 may comprise proximal end 402 and distal end 404. Internal recess 406 may be formed on distal end 404 of pressure cap 400. Pressure cap 400 may be configured to be disposed within body 300 and between a mounting rod and bone screw 100.

Internal recess 406 of pressure cap 400 may be formed on distal end 404 of pressure cap 400. Internal recess 406 may pass through from distal end 406 of pressure cap 404 to proximal end 402 of pressure cap 406. In some embodiments of the present disclosure, internal recess 406 may be configured to mate with external protrusion 106 of head 102 of bone screw 100. For example, in FIG. 4A, internal recess 406 may be configured to mate with external protrusion 106 of head 102 of bone screw 100. Mating of internal recess 406 with external protrusion 106 may limit movement of external protrusion 106 therein. In some embodiments of the present disclosure, internal recess 406 may be configured to allow substantial movement of external protrusion 106 of head 102 of bone screw 100. For example, in FIG. 4C, external protrusion 106 disposed within internal recess 406 may have substantially unrestricted movement. In some embodiments, external protrusion 106 may have poly-axial movement when disposed within internal recess 406.

The pressure cap 400 may be disposed above head 102 of bone screw 100. For internal recess 406 to mate with external protrusion 106, internal recess 406 may be formed on distal end 404 of pressure cap 400. Explained further, the recess that comprises internal recess 406 may begin at distal end 404 of pressure cap 406 and extend therein. Internal recess 406 may or may not extend all the way through to proximal end 402 of pressure cap 400. For example, FIG. 4A illustrates internal recess 406 with a hexagonal geometry that extends from distal end 404 to proximal end 402. Similarly, FIG. 4B illustrates internal recess 406 with a rectangular geometry that may extend from distal end 404 to proximal end 402. FIG. 4C illustrates internal recess 406 with a circular or cylindrical geometry that extends from distal end 404 to proximal end 402.

In some embodiments, internal recesses 406 of FIG. 4A, FIG. 4B, and FIG. 4C may not extend all the way through to proximal end 402 of pressure cap 400, but may still be operable to mate with external protrusion 106 of head 102 of bone screw 100. In such embodiments, proximal end 402 may comprise a covered surface with no recesses thereon. In such embodiments, internal recess 406 may not be visible from the perspective view of the pressure caps 400 as seen in FIG. 4A, FIG. 4B, and FIG. 4C. Various advantages may be achieved depending on whether or not internal recess 406 extends from distal end 406 of pressure cap 404 through proximal end 402 of pressure cap 406. For example, having internal recess 406 that extends all the way through to proximal end 402 may promote ease of selection among pressure caps with differently shaped internal recesses or may promote ease of handling of the pressure caps during a surgical procedure. Selection may be easier as it may be more efficient to visually determine which pressure cap 400 allows for a desired degree of movement. As another example, having internal recess 406 that does not extend all the way through to proximal end 402 may promote greater structure integrity.

Pressure cap 400 may further comprise at least one recess 408 disposed along outer surface 410 of pressure cap 400. As seen in FIG. 4A and FIG. 4B, in some embodiments, the at least one recess 408 may comprise a rectangular recess. In some embodiments the longer dimension of the rectangular geometry of the recess may be disposed substantially orthogonal to an axis formed by distal end 404 and proximal end 402. In some embodiments, pressure cap 400 may have a plurality of recesses 408 disposed along outer surface 410. In some embodiments, the plurality of recesses 408 may be spaced apart along outer surface 410. For example, in FIG. 4A and FIG. 4B, the pressure cap 400 may comprise a second recess on outer surface 410 that may be disposed opposite to first recess 408. An at least one recess 408 may allow pressure cap 400 to be more easily handled during surgical procedures. During surgical procedures, surgical instruments may be used to clamp the recesses and manipulate the positioning of pressure cap 400. For example, clamping the recesses with surgical instruments may allow pressure cap 400 to be more easily lowered into body 400 of the spinal fixation system. The surgical instruments may also be used to help align internal recess 406 of pressure cap 400 with external protrusion 106 in the desired manner or orientation. The number of recesses 408 or the positioning of recesses 408 along outer surface 410 may be varied without departing from the description herein.

In some embodiments, proximal end of pressure cap 400 may comprise a surface that may be partially curved so as to be operable to align with a portion of mounting rod 700 (see, for example, FIG. 7). Mounting rod 700 may be substantially cylindrical in geometry. Accordingly, the portion of the mounting rod 700 that may be biased against or pressed down upon pressure cap 400 in the fully assembled spinal fixation system may be curved. Accordingly, proximal end 402 of pressure cap 400 may be curved in a corresponding manner. As a result, a better fit may be achieved between proximal end 402 of the pressure cap 400 and the mounting rod 700. Mounting rod 700 selected for the spinal fixation system may have particular dimensions, radiuses, and curvature. Accordingly, the curvature of proximal surface of the pressure cap 400 may be varied in different embodiments to better accommodate or align with mounting rods 700 of different radiuses. Such variations in design may be made without departing from the description herein.

Figure 4D:
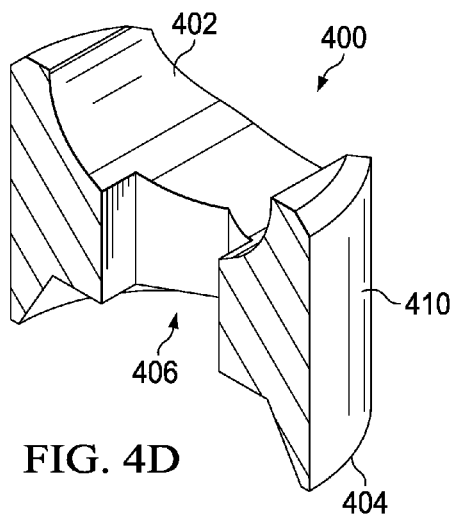
FIG. 4D illustrates a cross-sectional perspective view of a pressure cap according to an exemplary embodiment of the disclosure.
Figure 4E:
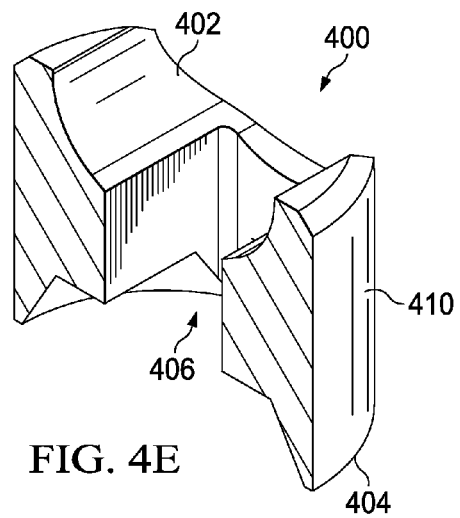
FIG. 4E illustrates a cross-sectional perspective view of a pressure cap according to an exemplary embodiment of the disclosure.
Figure 4F:
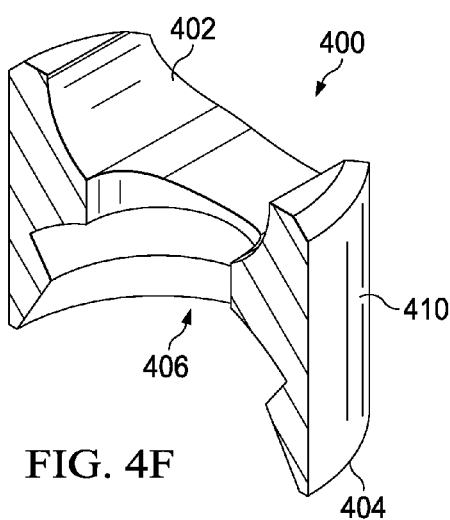
FIG. 4F illustrates a cross-sectional perspective view of a pressure cap according to an exemplary embodiment of the disclosure.

Referring to FIG. 4D, FIG. 4E, and FIG. 4F, cross-sectional perspective views of three exemplary pressure caps 400 according to specific example embodiments of the present disclosure are illustrated. An exemplary pressure cap 400 illustrated in FIG. 4D may be operable to limit the movement of bone screw 100 in a spinal fixation system to that of a mono-axial screw. An exemplary pressure cap 400 illustrated in FIG. 4E may be operable to limit the movement of bone screw 100 in a spinal fixation system to that of a uni-planar screw. An exemplary pressure cap 400 illustrated in FIG. 4F may be operable to allow for poly-axial movement of bone screw 100.

As seen in FIG. 4D, FIG. 4E, and FIG. 4F, pressure caps 400 may have proximal end 402, distal end 404, and outer surface 410. Internal recess 406 may be extended from proximal end 402 to distal end 404. As seen in FIG. 4D, FIG. 4E, and FIG. 4F, internal recess 406 may vary in size, shape, and/or geometry. Accordingly, internal recess 406 may allow for different degrees of movement or restrict movement of external protrusion 106 of head 102 of bone screw 100 that may be received therein.

Figure 5A:
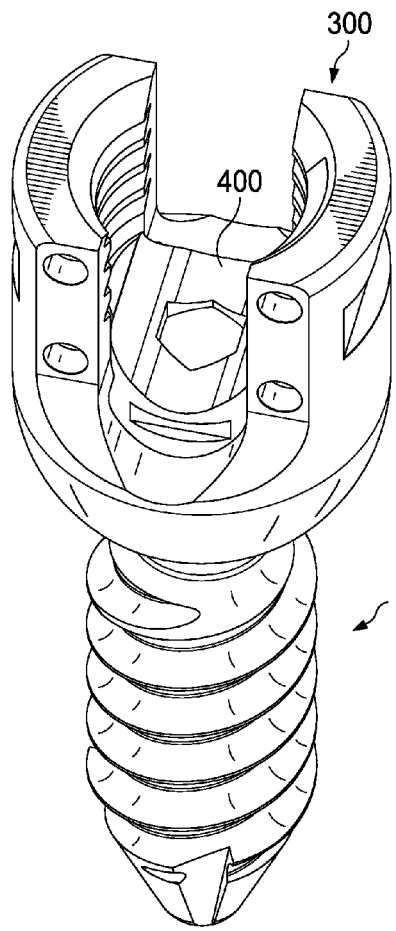
FIG. 5A illustrates a perspective view of a pressure cap, body, and bone screw fitted together according to an exemplary embodiment of the disclosure.
Figure 5B:
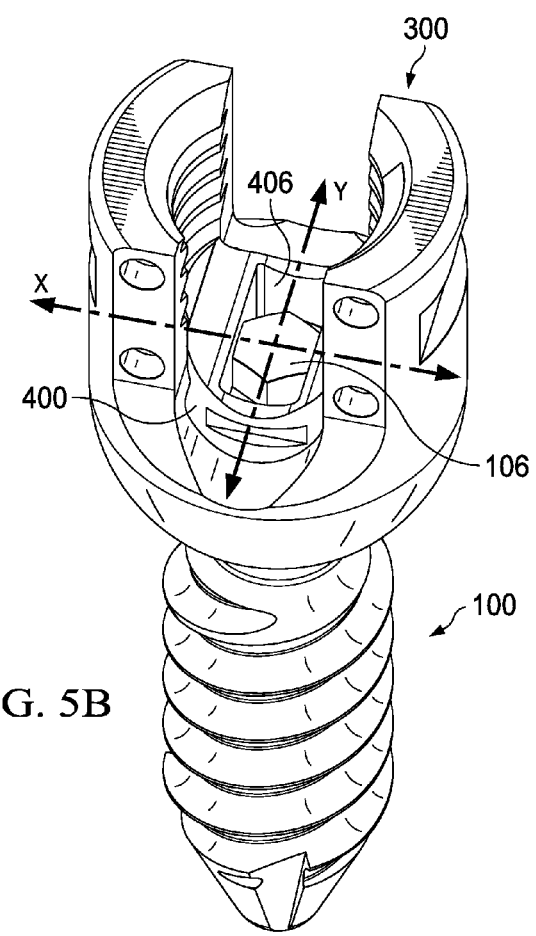
FIG. 5B illustrates a perspective view of a pressure cap, body, and bone screw fitted together according to an exemplary embodiment of the disclosure.
Figure 5C:
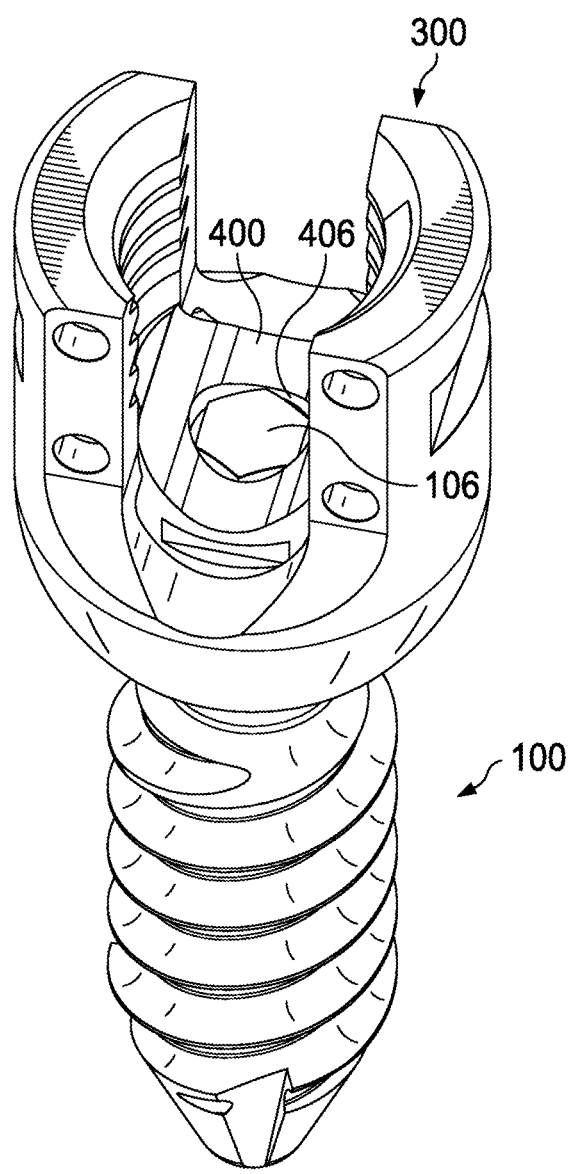
FIG. 5C illustrates a perspective view of a pressure cap, body, and bone screw fitted together according to an exemplary embodiment of the disclosure.
Figure 6A:
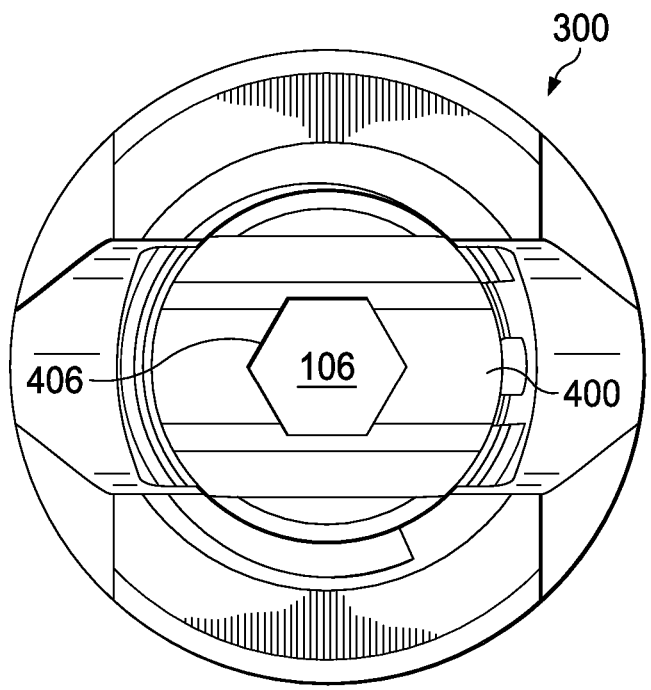
FIG. 6A illustrates a top-down view of a pressure cap, body, and bone screw fitted together according to an exemplary embodiment of the disclosure.
Figure 6B:
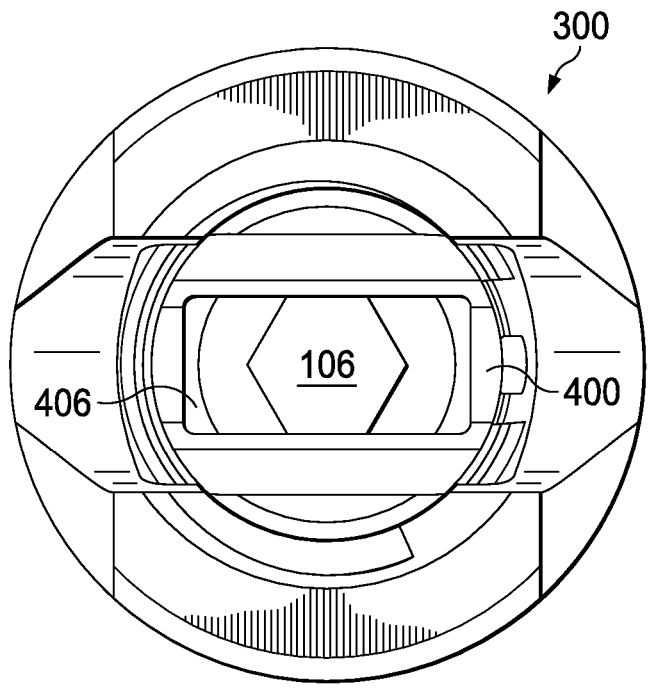
FIG. 6B illustrates a top-down view of a pressure cap, body, and bone screw fitted together according to an exemplary embodiment of the disclosure.

Referring to FIG. 5A, FIG. 5B, and FIG. 5C, perspective views of pressure cap 400, body 300, and bone screw 100 fitted together according to specific example embodiments of the present disclosure are illustrated. Referring to FIG. 6A and FIG. 6B, top-down views of pressure cap 400, body 300, and bone screw 100 fitted together according to specific example embodiments of the present disclosure are illustrated. Also depicted in FIG. 5A, FIG. 5B, FIG. 5C, FIG. 6A, and FIG. 6B, internal recess 406 of pressure cap 400 may be configured to mate with external protrusion 106 of head 102 of bone screw 100.

FIGS. 5A and 6A illustrate a pressure cap 400 fitted in body 300 and on bone screw 100 such that the movement of bone screw 100 in the spinal fixation system may be limited to that of a mono-axial screw. In some embodiments, internal recess 406 of pressure cap 400 may have a size or shape corresponding with external protrusion 106 of bone screw 100. Accordingly, when external protrusion 106 may be fitted into internal recess 406, lateral faces 112 of external protrusion 106 may be substantially or completely aligned with lateral faces of internal recess 406. Such a method of mating lateral faces 112 of external protrusion 106 with the shape of internal recess 406 may restrict the motion of bone screw 100. More specifically, the movement of bone screw 100 may be limited to that of a mono-axial screw. Described further, if one attempts to rotate or pivot bone screw 100 within body 300, certain lateral faces 112 of external protrusion 106 may be biased or pressured against a portion of the pressure cap 400. Accordingly, pressure cap 400 and internal recess 406 may serve to constrain bone screw 100 to one position.

FIGS. 5A and 6A illustrate pressure cap 400 with internal recess 406 that may have a hexagonal geometry and external protrusion 106 with a corresponding hexagonal geometry. Any number of polygonal geometries may be used to constrain bone screw 100 to the movement of a mono-axial screw. In some embodiments, the polygonal shape chosen for external protrusion 106 and internal recess 406 may be a triangle, rectangle, pentagon, heptagon, octagon, or star-shaped.

FIGS. 5B and 6B illustrate pressure cap 400 fitted in body 300 and on bone screw 100 such that the movement of bone screw 100 in the spinal fixation system may be limited to that of a uni-planar screw. In some embodiments, internal recess 306 of body 400 may comprise an elongated shape with a substantially rectangular geometry. In some embodiments, the rectangular geometry may have a width corresponding to a width of external protrusion 106 of bone screw 100. The length of the rectangular geometry may run substantially all the way along one direction of body 400. The depth of the rectangular geometry or internal recess 406 of body 400 may be sufficiently deep to allow internal recess 406 to receive external protrusion 106 of bone screw 100. In some embodiments, internal recess 406 sufficiently deep to receive external protrusion 106 may promote a more secure and stable mating of external protrusion 106 in internal recess 406.

In some embodiments, the width of the rectangular geometry of internal recess 406 that corresponds with a width of external protrusion 106 may serve to constrain external protrusion 106 and limit the movement of bone screw 100. Such a method of mating lateral faces 112 of external protrusion 106 with the shape of internal recess 406 may restrict the motion of bone screw 100 in all but one direction. More specifically, the movement of bone screw 100 may be limited to that of a uni-planar screw. Described further, if one attempts to rotate or pivot bone screw 100 within body 300, certain lateral faces 112 of external protrusion 106 may be biased or pressured against a portion of pressure cap 400. Accordingly, in some directions, bone screw 100 may be unable to rotate or pivot. However, in the direction of the length of internal recess 406, bone screw 100 may pivot while the external protrusion 106 may remain secure in internal recess 406.

In some embodiments, bone screw 100 may have a range of motion of approximately 35 degrees in each direction along the length of internal recess 406 where bone screw 100 and external protrusion 106 may pivot. Accordingly, in some embodiments, bone screw 100 may have a range of motion of approximately 70 degrees about a one axis of movement. The range of motion of such a uni-planar screw may be varied without departing from the description herein. The range of motion may be changed, for example, by adjusting the length or dimensions of internal recess 406, adjusting the ball bearing design at screw head 102 region of bone screw 100, or adjusting geometry and dimensions of external protrusion 106.

As seen in FIG. 5B, an exemplary embodiment of a modular pedicle screw configured to allow for uni-planar movement may allow the bone screw to move along the Y axis. In FIG. 5B, the illustrated embodiment of the present disclosure may include bone screw 100 with external protrusion 106 fitted in internal recess 406 of pressure cap 400. External protrusion 106 may pivot within internal recess 406 such that bone screw 100 may have a limited range of motion along the Y axis. Further, internal recess 406 may be configured such that movement in other directions other than the Y axis, such as the X axis, may be completely restricted. In the exemplary embodiment of FIG. 5B, movement of bone screw 100 in the X axis may be restricted as a result of certain lateral faces 112 being biased or pressured against walls of internal recess 406 of pressure cap 400.

In some embodiments, internal recess 406 may have a height of about 2 mm to about 5 mm. A height of internal recess 406 may match with a dimension of external protrusion 106. The dimensions of internal recess 406 may be varied to achieve various functional objections and may be varied without departing from the description herein. For example, bone screw 100 used for the cervical and upper thoracic regions may have smaller internal recess 406. As another example, bone screw 100 used for the lumbar or lower thoracic regions may have larger internal recess 406. The dimensions of the internal recess 406 may be varied so that internal recess 406 may more securely receive external protrusion 106 of bone screw 100.

FIG. 5C illustrates a pressure cap 400 fitted in body 300 and on bone screw 100 such that the movement of bone screw 100 in the spinal fixation system may be relatively unrestricted or substantially unrestricted. In some embodiments, bone screw 100 may retain poly-axial movement within the internal recess 406 of pressure cap 400. Movement of bone screw 100 may be limited by pressure cap 400. For example, degree of movement along each axis may be reduced. However, poly-axial movement may advantageously be retained. In some surgical situations, providing for poly-axial movement but reducing the degree of movement in each direction may be advantageous. Reduced range of movement may provide added security and stability to a bone screw system or bone screw assembly. Disposing pressure cap 400 on bone screw 100 may provide a compressive force on bone screw 100. Compressive forces applied on bone screw 100 may advantageously provide for a more secure bone screw system or bone screw assembly.

Pressure caps 400 of the present disclosure may be conveniently interchanged. For example, a surgeon may select pressure cap 400 that may limit bone screw 100 to mono-axial movement. However, upon fitting said pressure cap 400 on bone screw 100 in body 300, the surgeon may realize that a greater degree of movement may be advantageous. Accordingly, the surgeon may remove pressure cap 400 from body 300. The removal may be performed by using surgical instruments to clasp or grip recesses 408 disposed along outer surface of pressure cap 400. Said recesses 408 may be positioned in body 300 such that they are exposed by the opening of mounting rod receiving channel 306. Thus, said recesses 408 may be easily reachable with surgical instrument, and may promote the removal of the entire pressure cap 400 from body 300. The surgeon may then place a different pressure cap that may be more appropriate in size, design, or the degree of movement that it allows the bone screw. For example, a surgeon may determine that a screw with uni-planar movement or poly-axial movement may be more appropriate in the particular setting to allow for proper alignment of the mounting rod as disposed between a plurality of bodies 300 in a spinal fixation system. Accordingly, the surgeon may select pressure cap 400 and fit it into the body 300 so that it may be secured over bone screw 100. The fitting may be such that external protrusion 106 of the bone screw 100 may be securely received into internal recess 406 of body 400.

This selection process, as promoted by the interchangeability of the pressure caps, may be repeated as many times as necessary to achieve the most appropriate fitting for a particular surgical situation. For example, after replacing pressure cap 400 that may allow for mono-axial movement with pressure cap 400 that may allow for uni-planar movement, the surgeon may decide that pressure cap 400 allowing for mono-axial movement may have provided a better fit and better stability. Accordingly, the surgeon may swap out pressure cap 400 with uni-planar movement for a pressure cap 400 with mono-axial movement. As another example, after one instance of interchanging the pressure cap, the surgeon may decide that a pressure cap allowing for poly-axial movement may be more advantageous in a particular surgical setting. Thus, the surgeon may swap out the currently fitted pressure cap with yet another, re-selected pressure cap.

Figure 8:
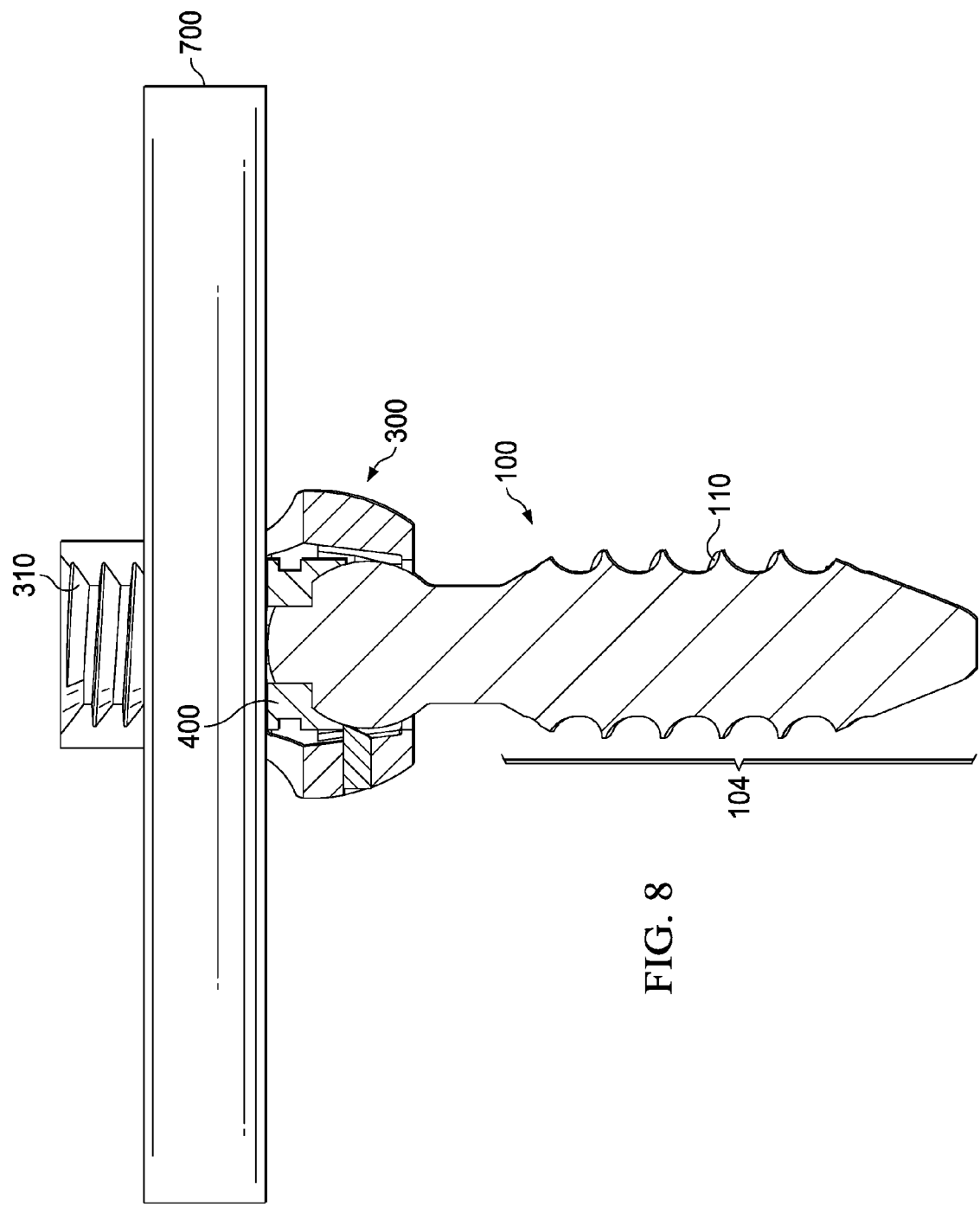
FIG. 8 illustrates a profile view of a mounting rod, pressure cap, body, and bone screw fitted together according to an exemplary embodiment of the disclosure.

Referring to FIG. 7, a perspective view of mounting rod 700, pressure cap 400, body 300, and bone screw 100 fitted together according to a specific example embodiment of the disclosure is illustrated. Referring to FIG. 8, a profile view of mounting rod 700, pressure cap 400, body 300, and bone screw 100 fitted together according to a specific example embodiment of the disclosure is illustrated. FIG. 7 and FIG. 8 illustrate how exemplary embodiments of the present disclosure may be assembled as part of a spinal fixation system. As seen in FIG. 7 and FIG. 8, the spinal fixation system may comprise bone screw 100 that may be fitted into body 300. Bone screw 100 may comprise bone connection element 104 with external thread 100 operable for being fastened or screwed into a bone. A spinal fixation system may then be fitted with selected pressure cap 400. Then, mounting rod 700 may be disposed or placed into the body through mounting rod receiving channel 306. Mounting rod 700 may be disposed in such a manner such that a proximal portion comprising internal thread 310 may be exposed and may be operable to receive a compression element.

In some embodiments, pressure cap 400 may be operable to exert pressure on bone screw 100 when mounting rod 700 is biased against the proximal end of the pressure cap 400. Mounting rod 700 may be biased or pressed down against proximal end 402 of pressure cap 400 when the compression element is securely fastened or screwed into internal threads 310 of body 300. The pressure that may be created from the fastening of the compression element and from mounting rod 700 being biased or pressed down on pressure cap 400 and bone screw 100, may create a secure and stable assembly as part of the spinal fixation system.

Modular pedicle screws of the present disclosure may encompass various embodiments without departing from the description herein. The present disclosure relates, in some embodiments, to bone screws that may comprise an internal recess disposed on the head of a bone screw. In such embodiments, a pressure cap may comprise an external protrusion formed on a distal end of a pressure cap. Such embodiments differ from the previously described embodiments in that an external member may be located on a pressure cap while an internal recess or the receiving spacing for an external member may be located on a bone screw. In the presently described embodiments, a secure fit may also be achieved between an internal recess of a bone screw and an external protrusion of a pressure cap.

Furthermore, an internal recess of a bone screw and an external protrusion of a pressure cap may be designed so as to limit the movement of a bone screw. For example, in some embodiments, an internal recess of a bone screw may be designed and configured to limit the movement of a bone screw to that of a mono-axial screw. In such embodiments, an internal recess of a bone screw may comprise a geometry that substantially corresponds with the geometry formed by a cross-section of a plurality of lateral faces that comprise an external protrusion of a pressure cap. Accordingly, the movement of an external protrusion of a pressure cap, and movement of a bone screw along with it, may be confined to that of a mono-axial screw.

In some embodiments, an internal recess of a bone screw may be an elongated recess that may be disposed on the head of a bone screw. Accordingly, an external protrusion may have movement that may be limited to pivotal movement about one axis. In some embodiments, the movement of a bone screw may be limited to about 35 degrees in either direction of pivotal movement about a one axis where movement may be allowed. Described further, in some embodiments, a bone screw may be limited to about 70 degrees of pivotal movement along a one axis where movement may be allowed.

Still further, one of ordinary skill in the art would appreciate that any of the features, variations, and other embodiments described above for the configuration that may comprise an external protrusion 106 on a bone screw 100 and an internal recess 406 on a pressure cap 400, may also be applied for the configuration that may comprise an internal recess on the bone screw and an external protrusion on the pressure cap. Any of the previously descried features or variations may be made but for a reversal of the placement of an external protrusion 106 and an internal recess 406.

In any of the embodiments of the present disclosure, the materials may be chosen and may be varied to fit a number of functional and design considerations. In some embodiments, bone screw 100, body, 300, pressure cap 400, mounting rod 700, and compression element may be made of materials such as Titanium, Ti-6Al-4V, stainless steel or CoCr. However, any implantable metallic material may be used without departing from the description herein. Furthermore, a material for each component may be independently selected and a material of each component may vary from one another without departing from the description herein.

The present disclosure relates, in some embodiments, to methods of affixing a bone screw system to a bone. The method may comprise fitting bone screw 100 to body 300. Bone screw 100 may comprise head 102 at a proximal end, bone connection element 104 at a distal end, and external protrusion 106 disposed on the head 102 of the bone screw 100. Body 300 may comprise proximal end 302, distal end 304, mounting rod receiving channel 306 disposed at proximal end 302 of body 300, and bone screw head receiving channel 308 disposed at distal end 304 of body 300. Proximal end 302 and distal end 304 may be disposed along a longitudinal axis. In assembling a bone screw system, bone screw 100 may be inserted through mounting rod receiving channel 306 of body 300 such that head 302 may be received and may sit securely in the bone screw head receiving channel 308.

Bone connection element 104 of bone screw 100 may be fastened or screwed into a bone. The securing of the bone screw may be done through a number of mechanical means.

Either before, after, or while bone connection element 104 is secured into a bone, pressure cap 400 may be selected. The selection may be made based on the desired degree of stability of desired degree of movement allowed for bone screw 100. Pressure cap may comprise proximal end 402, distal end 404, and internal recess 406 formed on the distal end 404 of pressure cap 400. Internal recess 406 may be configured to mate with the external protrusion 106 of bone screw 100 so as to limit the movement of bone screw 100.

Pressure cap 400 may be fitted on or fitted against head 102 of bone screw 100 within the body. The mating of external protrusion 106 and internal recess 406 may serve to limit the movement of bone screw 100

Next, mounting rod 700 may be disposed within body 300. Mounting rod 700 may be fitted within mounting rod receiving channel 306. Mounting rod 700 may be disposed against proximate end 402 of pressure cap 400.

Then, a compression element may be secured within mounting rod receiving channel 306. The securing of the compression element may create a compressive force on mounting rod 700 that may allow mounting rod 500 to biased against or be pressed down on pressure cap 400. The resulting compressive forces may promote a more secure and stable assembly or spinal fixation system. Any of the features, variations, and other embodiments described above for the articles and systems of the present disclosure may apply to the presently disclosed methods without departing from there description herein.

As will be understood by those skilled in the art who have the benefit of the instant disclosure, other equivalent or alternative compositions, devices, methods, and systems for a modular pedicle screw can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/− about 10%, depicted value+/− about 50%, depicted value+/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for a modular pedicle screw may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A spinal fixation system, comprising:
   at least one bone screw comprising:
      a head at a proximal end;
      a bone connection element at a distal end; and
      an external protrusion disposed on the head of the bone screw;
   at least one body comprising:
      a proximal end and a distal end disposed along a longitudinal axis;

a mounting rod receiving channel disposed at the proximal end of the body; and a bone screw head receiving channel disposed at the distal end of the body;

wherein a proximal portion of the mounting rod receiving channel comprises an internal thread operable to receive a compression element; and at least one pressure cap comprising:

a proximal end;

a distal end;

an internal recess formed on the distal end of the pressure cap; and at least one recess disposed along an outer surface of the pressure cap, the outer surface being a side surface between the proximal end and the distal end, and the recess being spaced from the proximal end of the pressure cap such that a non-recessed region is disposed between the recess and the proximal end of the pressure cap;

wherein the pressure cap is operable to be disposed within the body and between a mounting rod and the bone screw;

wherein the pressure cap is operable to exert pressure on the head of the bone screw when the mounting rod is biased against the proximal end of the pressure cap;

wherein the at least one recess disposed along the outer surface of the pressure cap is externally accessible via the mounting rod receiving channel when the pressure cap is disposed within the body and in contact with the bone screw;

wherein the internal recess is operable to mate with the external protrusion of the bone screw so as to limit the movement of the bone screw: and wherein the recess extends in a circumferential direction about the pressure cap.

2. The spinal fixation system according to claim 1, wherein the head of the bone screw has a substantially spherical surface.

3. The spinal fixation system according to claim 1, wherein the bone connection element comprises an external thread operable to be secured into a pedicle portion of a spine.

4. The spinal fixation system according to claim 1, wherein the bone connection element has a diameter of about 2.5 mm to about 9 mm.

5. The spinal fixation system according to claim 1, wherein the bone connection element has a length of about 6 mm to 120 mm.

6. The spinal fixation system according to claim 1, wherein the external protrusion has a plurality of lateral faces forming a cross-section with a polygonal shape.

7. The spinal fixation system according to claim 6, wherein the polygonal shape is selected from the group consisting of a triangle, rectangle, pentagon, hexagon, heptagon, octagon, or star.

8. The spinal fixation system according to claim 1, wherein the external protrusion has a height of about 2 mm to about 5 mm.

9. The spinal fixation system according to claim 1, wherein the mounting rod receiving channel is operable to receive the mounting rod at an angle substantially orthogonal to the longitudinal axis of the body.

10. The spinal fixation system according to claim 1, wherein the bone screw head receiving channel is sized to securely receive the bone screw head.

11. The spinal fixation system according to claim 1, wherein the proximal end of the pressure cap comprises a surface that is partially curved and operable to align with a portion of the mounting rod.

12. The spinal fixation system according to claim 1, wherein the internal recess passes through from the distal end of the pressure cap to the proximal end of the pressure cap.

13. The spinal fixation system according to claim 1, wherein the bone screw, the body, the compression element, and the pressure cap each comprises a material independently selected from the group consisting of titanium, titanium alloy, stainless steel, cobalt chrome, and any combination thereof.

14. The spinal fixation system according to claim 1, wherein the internal recess is operable to limit the movement of the bone screw to that of a mono-axial screw.

15. The spinal fixation system according to claim 1, wherein the internal recess limits the pivotal movement of the bone screw to one axis.

16. The spinal fixation system according to claim 15, wherein the bone screw has about 70 degrees of pivotal movement about the one axis.

17. The spinal fixation system according to claim 15, wherein the internal recess has a rectangular shape with a width corresponding to a width of the external protrusion, and a depth sufficient to allow the internal recess to receive the external protrusion.

18. The spinal fixation system according to claim 1, wherein the internal recess is operable to mate with the external protrusion of the bone screw to allow poly-axial movement of the bone screw.

19. The spinal fixation system according to claim 1, wherein the recess disposed along the outer surface of the pressure cap extends a first distance in the circumferential direction about the pressure cap, the recess disposed along the outer surface of the pressure cap extends a second distance in an axial direction about the pressure cap, and the first distance is greater than the second distance.

20. The spinal fixation system according to claim 1, wherein the external protrusion has a diameter smaller than a diameter of the head of the bone screw.

21. A spinal fixation system, comprising:

at least one bone screw comprising:

a head at a proximal end;

a bone connection element at a distal end; and an internal recess disposed on the head of the bone screw;

at least one body comprising:

a proximal end and a distal end disposed along a longitudinal axis;

a mounting rod receiving channel disposed at the proximal end of the body;

a bone screw head receiving channel disposed at the distal end of the body;

wherein a proximal portion of the mounting rod receiving channel comprises an internal thread operable to receive a compression element; and at least one pressure cap comprising:

a proximal end;

a distal end;

an external protrusion formed on the distal end of the pressure cap; and at least one recess disposed along an outer surface of the pressure cap, the outer surface being a side surface between the proximal end and the distal end, the recess being spaced from the proximal end of the pressure cap such that a non-recessed region is disposed between the recess and the proximal end of the pressure cap;

wherein the pressure cap is operable to be disposed within the body and between a mounting rod and the bone screw;

wherein the pressure cap is operable to exert pressure on the head of the bone screw when the mounting rod is biased against the proximal end of the pressure cap;

wherein the at least one recess disposed along the outer surface of the pressure cap is externally accessible via the mounting rod receiving channel when the pressure cap is disposed within the body and in contact with the bone screw;

wherein the external protrusion is configured to mate with the internal recess of the bone screw so as to limit the movement of the bone screw: and wherein the recess extends in a circumferential direction about the pressure cap.

22. The spinal fixation system according to claim 21, wherein the head of the bone screw has a substantially spherical surface.

23. The spinal fixation system according to claim 21, wherein the bone connection element comprises an external thread operable to be secured into a pedicle portion of a spine.

24. The spinal fixation system according to claim 21, wherein the bone connection element has a diameter of about 2.5 mm to about 9 mm.

25. The spinal fixation system according to claim 21, wherein the bone connection element has a length of about 6 mm to 120 mm.

26. The spinal fixation system according to claim 21, wherein the internal recess has a plurality of lateral faces forming a cross-section with a polygonal shape.

27. The spinal fixation system according to claim 21, wherein the polygonal shape is selected from the group consisting of a triangle, rectangle, pentagon, hexagon, heptagon, octagon, or star.

28. The spinal fixation system according to claim 21, wherein the internal recess has a height of about 2 mm to about 5 mm.

29. The spinal fixation system according to claim 21, wherein the mounting rod receiving channel is operable to receive the mounting rod at an angle substantially orthogonal to the longitudinal axis of the body.

30. The spinal fixation system according to claim 21, wherein the bone screw head receiving channel is sized to securely receive the bone screw head.

31. The spinal fixation system according to claim 21, wherein the proximal end of the pressure cap comprises a surface that is partially curved and operable to align with a portion of the mounting rod.

32. The spinal fixation system according to claim 21, wherein the bone screw, the body, the compression element, and the pressure cap each comprises a material independently selected from the group consisting of titanium, titanium alloy, stainless steel, cobalt chrome, and any combination thereof.

33. The spinal fixation system according to claim 21, wherein the external protrusion is configured to limit the movement of the bone screw to that of a mono-axial screw.

34. The spinal fixation system according to claim 21, wherein the external protrusion limits the pivotal movement of the bone screw to one axis.

35. The spinal fixation system according to claim 34, wherein the bone screw has about 70 degrees of pivotal movement about the one axis.

36. The spinal fixation system according to claim 34, wherein the external protrusion has a rectangular shape with a width corresponding to a width of the internal recess, and a depth sufficient to allow the internal recess to receive the external protrusion.

37. The spinal fixation system according to claim 21, wherein the external protrusion is configured to mate with the external protrusion of the bone screw to allow poly-axial movement of the bone screw.

38. A method of affixing a bone screw system, the method comprising:
fitting a bone screw within a body,
wherein the bone screw comprises:
a head at a proximal end;
a bone connection element at a distal end; and
an external protrusion disposed on the head of the bone screw;
wherein the body comprises:
a proximal end and a distal end disposed along a longitudinal axis;
a mounting rod receiving channel disposed at the proximal end of the body; and
a bone screw head receiving channel disposed at the distal end of the body;
securing the bone connection element in a bone;
selecting a pressure cap,
wherein the pressure cap comprises:
a proximal end;
a distal end;
an internal recess formed on the distal end of the pressure cap; and
at least one recess disposed along an outer surface of the pressure cap, the outer surface being a side surface between the proximal end and the distal end, and the recess being spaced from the proximal end of the pressure cap such that a non-recessed region is disposed between the recess and the proximal end of the pressure cap;
wherein the pressure cap is operable to exert pressure on the head of the bone screw when a mounting rod is biased against the proximal end of the pressure cap;
wherein the at least one recess disposed along the outer surface of the pressure cap is externally accessible via the mounting rod receiving channel when the pressure cap is disposed within the body and in contact with the bone screw; and
wherein the internal recess is operable to mate with the external protrusion of the bone screw so as to limit the movement of the bone screw;
fitting the pressure cap against the head of the bone screw within the body;
fitting the mounting rod within the mounting rod receiving channel so that the rod is disposed against the proximate end of the pressure cap; and
securing a compression element within the mounting rod receiving channel so that a bias is applied by the pressure cap against the head of the bone screw, wherein the recess extends in a circumferential direction about the pressure cab.

* * * * *